(12) United States Patent
Weber et al.

(10) Patent No.: US 6,226,996 B1
(45) Date of Patent: May 8, 2001

(54) DEVICE FOR CONTROLLED COOLING OF A SURFACE

(76) Inventors: Paul J. Weber, 1 Seasame Rd., Sea Ranch Lakes, FL (US) 33308; Robert S. Bader, 5547 N. Military Trail, #2401, Boca Raton, FL (US) 33496; Luiz B. Da Silva, 6270 Stoneridge Mall Rd. Apt. C214, Pleasanton, CA (US) 94588

( * ) Notice: Subject to any disclaimer, the term of this patent is extended or adjusted under 35 U.S.C. 154(b) by 0 days.

(21) Appl. No.: 09/413,377

(22) Filed: Oct. 6, 1999

(51) Int. Cl.[7] ........................................... F17C 7/04
(52) U.S. Cl. ..................... 62/126; 62/52.1; 236/51; 606/22
(58) Field of Search ........................... 62/126, 93 R, 62/94, 64, 52.1; 128/200.14; 236/51, 93 R, 94; 606/20, 22

(56) References Cited

U.S. PATENT DOCUMENTS

| | | | |
|---|---|---|---|
| 3,534,739 | * 10/1970 | Bryne | 128/303.1 |
| 3,651,813 | * 3/1972 | Bryne | 128/303.1 |
| 4,043,341 | * 8/1977 | Tromovitch | 128/303.1 |
| 4,116,199 | 9/1978 | Bryne . | |
| 4,348,873 | * 9/1982 | Yamauchi et al. | 62/514 R |
| 5,098,428 | * 3/1992 | Sandlin et al. | 606/22 |
| 5,814,040 | * 9/1998 | Nelson et al. | 606/9 |

* cited by examiner

Primary Examiner—Harry B. Tanner
(74) Attorney, Agent, or Firm—John P. Wooldridge

(57) ABSTRACT

A device is described that uniformly cools a surface to a specified temperature using a mist of cryogenic fluid. The device comprises a cryogenic fluid reservoir, a valve for controllably releasing the fluid through an atomizing nozzle, a non-contact temperature sensor, and a control unit to display the measured temperature and optionally pre-set the desired surface temperature and control the valve. The application of mist can be controlled manually or electronically. This invention provides a portable tool for safely cooling skin for dermatological applications.

39 Claims, 3 Drawing Sheets

DEVICE FOR CONTROLLED COOLING OF A SURFACE

BACKGROUND OF THE INVENTION

1. Field of the Invention

The present invention relates to a device for uniformly cooling a surface, such as human skin, to a specified temperature using a cold mist of a cryogenic fluid and a non-contact temperature sensor.

2. Description of Related Art

The use of liquified gas coolants to cool and freeze tissue has long been known. For example, dichlorotetrafluoroethane (also known as Frigiderm® or Freon 114) has been used extensively in cosmetic surgery to cool and stiffen skin properly before mechanical dermabrasion with a rotating abrasive wheel.

The hardness of the skin freeze has been shown to be critical in controlling the depth of dermabrasion and classified as either superficial (0.2–0.5 mm), moderate (0.5–1.0 mm), or deep (1.5–2.0 mm) according to Ayres {Ayres S III: Superficial chemosurgery, including combined technique, using dermabrasion, in Epstein E, Epstein E Jr, editors: Skin surgery. Springfield, Ill., 1982, Charles C Thomas, Publisher.} The skin temperatures achieved and thus the hardness of the skin is dependent upon the type of freezing agent, skin temperature prior to treatment, operating room temperature, distance of spray, pressure of spray, density of spray, angle of spray and time of spray, among other variables.

The advantage of dichlorotetrafluoroethane is that under normal conditions its maximum skin cooling temperatures is −40° C., even though its boiling point is +3.8° C. Ethyl chloride was an efficient skin refrigerant but had the undesirable qualities of being explosive when mixed with air, toxic to the liver, as well as capable of causing general anesthesia upon inhalation by the patient or doctor.

It has been proven that colder cryorefrigerants (ie Cryosthesia −60° C. also known as dichlorodifluoromethane or Freon 12, boiling point −29.8° C.) can produce maximum skin cooling temperatures of −66° C. causing unwanted tissue damage and resulting in serious complications (scarring, depigmentation, infection).

Unfortunately, all of these chlorofluorocarbon refrigerants have been shown to damage the ozone layer and their use is now strictly controlled if not outright banned in many countries.

Dry ice or frozen carbon dioxide has also been used to cool the skin. However, applying dry ice to the skin's surface can quickly produce temperatures of close to −78° C. "Dry ice" application has been shown to be destructive to the epithelium layer and is now more commonly used to improve the penetration of skin peeling chemicals by removing the epidermis just prior to peel-acid application. Because temperatures of −78° C. are rapidly approached with little room for manual control, direct solid state, "dry ice" contact is not a viable option for controlled cooling of skin prior to or during dermabrasion if the surgeon is to minimize thermal damage. Surgeons have reported that solid carbon dioxide contact produced scarring because it was applied under pressure that occluded the, otherwise warming, local blood supply.

Cryogenic fluids such as liquid nitrogen, which pose little risk to the environment, have also been used extensively to cool surfaces. However, when sprayed on surfaces liquid nitrogen can quickly produce surface temperatures as low as −196° C. Unfortunately, for many applications and in particular cosmetic surgery this low temperature can seriously damage and kill human tissue.

Given the disadvantages of current human skin cooling techniques, a need exists for a device that provides a safe and economical alternative. The present invention uses a cryogenic mist and non-contact temperature sensor to cool a surface to a desired temperature. By using a cryogenic mist, the cooling can be maintained at safe levels that allow the user to either electronically or manually control the cooling process.

SUMMARY OF THE INVENTION

The object of the present invention is to provide a device that can uniformly cool a surface to a specified temperature using a cold gas or mist. The device comprises a reservoir for a cryogenic fluid, a valve for controllably releasing the fluid through an atomizing nozzle, a non-contact temperature sensor, and an electronic control unit to display the temperature values and optionally control the valve. It is further an object of this invention to provide a tool for safely cooling skin for performing dermabration without using chlorofluorocarbon gas.

In one embodiment of the present invention, the user sets the desired temperature on the electronic control unit using a touch pad or other user interface. The device is then directed at the target surface, and the valve is opened manually or electronically by pressing a button, switch, or lever. The cryogenic fluid in the reservoir flows through the valve and exits an atomizing nozzle, where the liquid is turned into a gas or mist of small droplets (aerosol) that can evaporate as they propagate towards the target surface. The cryogenic fluid can be any low temperature liquid or gas, for example, nitrogen, helium, xenon, carbon dioxide, chlorofluorocarbon (CFC) refrigerants or the many low temperature alternatives to CFC's.

The surface temperature of the area being exposed to the cold mist is measured with a non-contact temperature sensor, and the value is displayed on the control unit, such as on a liquid crystal display. The control unit may be programmed to produce an audible or optical alarm or signal when the measured temperature reaches the desired (pre-set) temperature. At this point, the user manually closes the valve, thereby stopping the fluid flow and cooling. Alternatively, the control unit may be programmed to automatically close an electronic valve when the desired temperature is reached, thereby eliminating the need for the user to manually operate the valve and providing a safety mechanism.

The cryogenic reservoir can be any one of a variety of reservoirs that are commercially available or known in the art (e.g., U.S. Pat. No. 4,116,199). The cryogenic reservoir operating pressure and atomizing nozzle are selected to produce a fine mist that uniformly cools the surface over a desired area. The device uses a non-contact temperature sensor to avoid perturbing the surface. The preferred non-contact temperature sensor is an infrared temperature sensor, but could include other sensors such as fluorescence temperature sensors. Since most non-contact temperature sensors average the temperature over a specified field, it is important that the cooled area overlaps the area sampled by the temperature sensor. To that end, a properly aligned optical source that generates an optical beam or pattern may be added to identify a spot or area where the temperature is measured.

The present invention is useful for cooling human or animal skin for dermatological applications, such as dermabrasion. Other applications include cooling metal surfaces for assembly or surface conditioning. The foregoing and other objects, features and advantages of the present invention will become apparent from the following description and accompanying drawings.

BRIEF DESCRIPTION OF THE DRAWINGS

The accompanying drawings, which are incorporated into and form part of this disclosure, illustrate embodiments of the invention and together with the description, serve to explain the principles of the invention.

DETAILED DESCRIPTION OF THE INVENTION

The present invention provides a device that can uniformly cool a surface to a specified temperature using a cold gas or mist. The device comprises a reservoir for a cryogenic fluid, a valve for releasing the fluid through an atomizing nozzle, a non-contact temperature sensor, and an electronic control unit to display the temperature values and optionally control the valve. This invention provides a portable tool for safely cooling the skin prior to performing dermabration without using freon gas.

Figure 1:
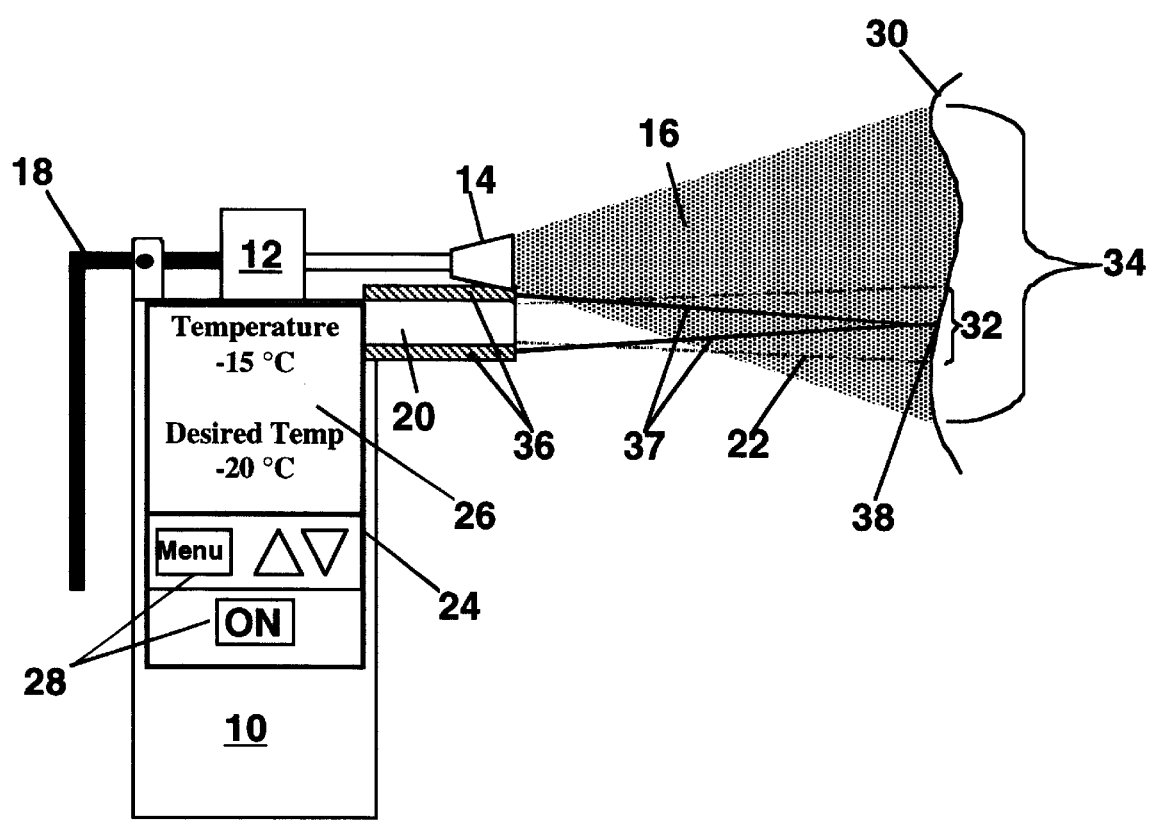
FIG. 1 shows an embodiment of the device according to the present invention.

FIG. 1 shows an embodiment of the device according to the present invention. The device comprises a cryogenic fluid reservoir 10, where the flow of fluid out of the reservoir is controlled by a cryogenic valve 12. The valve 12 is opened manually by pressing a handle or lever 18. When the valve 12 is open, the cryogenic fluid can flow up through the valve 12 and the atomizing nozzle 14, where it is converted into a mist 16 (or aerosol). For the purposes of this invention, a mist is defined as a mixture of gas and small liquid droplets. The atomizing nozzle 14 can comprise a single orifice or a plurality of small orifices designed to produce optimum size droplets and a uniform mist over a targeted area. The mist 16 expands away from the nozzle 14 and impacts the target surface 30 over a certain area 34 to be cooled. The nozzle 14 can be adjusted to enlarge or reduce the area 34 to be cooled, or the nozzle 14 to surface 30 distance can be adjusted. The choice of cryogenic fluid, such nitrogen, helium, or xenon, depends on the specific application.

An electronic control unit 24 is connected to the reservoir 10. The control unit 24 includes a display 26, such as a liquid crystal display, and a user interface 28, such as a touch pad with keys, buttons or switches. The interface 28 and display 24 allow the user to pre-set or program the desired final surface 30 temperature, activate the temperature sensor 20, and continuously monitor the surface 30 temperature. The display 26 is situated on the device so that the user may observe the change in temperature during operation of the device. The interface 28 and display 26 can be designed to provide information or options for other various features, e.g., alarms, optical beam alignment of the sensor 20, or fluid level in the cryogenic reservoir 10.

A non-contact temperature sensor 20 is connected to the control unit 24. The preferred temperature sensor is an infrared sensor (e.g., Omega Engineering, Inc. OS36), but other conventional sensors may be used, such as a fluorescence temperature sensor. The sensor 20 monitors the temperature within the surface area 32 on the target surface 30 intersected by a virtual cone or field of view defined by 22. The area 32 sampled by the temperature sensor 20 must be within the cooled area 34 to acquire accurate measurements. To prevent possible damage to the surface, the uniformity of cooling over the sampled region 32 must be sufficient to limit any possible temperature error to acceptable levels.

The distance between the nozzle 14 and the surface 30 is such that the surface is uniformly cooled over an area 34 larger than or equivalent to the area 32 sampled by the temperature sensor 20. The position of the temperature sensor 20 can be adjusted to intercept the cooling mist 16 over a wide range of nozzle 14 to surface 30 distances. The sensor 20 should be situated on the device so as to not physically interfere with, block, or perturb the mist 16. The mist 16 has little or no affect on the measurements of the surface 30 by the temperature sensor 20, as the mist is effectively transparent to the sensor 20.

As an optional feature, an optical source 36 (e.g. an LED coupled to one or multiple fiber optics and lenses) can be incorporated into or attached to the device (e.g., on the temperature sensor 20 as shown) to produce one or a plurality of optical beams 37 that illuminates a point 38. By using at least two beams that are aligned to intersect at point 38, the user can also use the optical beams to accurately position the device at the optimum distance from the surface. Alternatively the optical source can produce a broad beam pattern that illuminates the total area 32 monitored by the sensor. Alternatively or in addition, an optical source can be located so as to illuminate the boundary or the total area 34 covered by the nozzle mist so that the size of the affected (cooled) area can be verified before applying the mist.

While the surface 30 is being cooled, the measured temperature is continuously displayed on the display 26. When the measured temperature reaches the desired value, the user then closes the valve 12 by releasing the lever 18. An audible or optical alarm or visual alert may optionally be generated by the control unit 24 when the measured temperature reaches the desired temperature. The control unit 24 and temperature sensor 20 may be battery or DC or AC powered.

Figure 2:
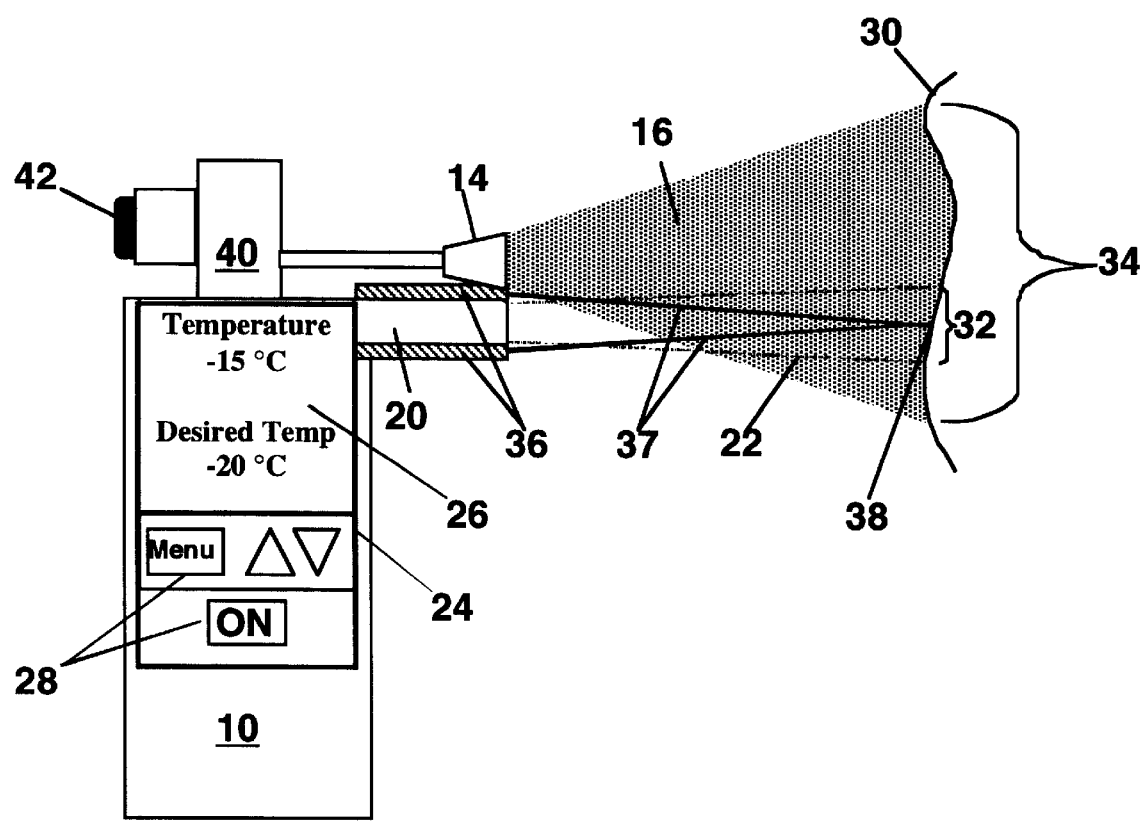
FIG. 2 shows an alternative embodiment of the device.

FIG. 2 shows an alternative embodiment of the device according to the present invention. In this embodiment, the manual valve 12 shown in FIG. 1 is replaced by an electronic valve 40 that is controlled by the control unit 24. The valve 40 is opened when the user presses a switch, lever, pedal, or button 42. To avoid having the user continuously depress a button during operation, the valve 40 can be closed when the switch or button 42 is pressed again. The button or switch 42 should be situated on the device so that the user can easily reach it with a thumb or finger. The control unit 24 can also be set or programmed to automatically close the valve 42 when the surface 30 temperature reaches the desired temperature set by the user. The control unit 24 may have an automatic shut-off safety feature that prevents the user from exceeding certain time or temperature parameters that may damage a surface, such as skin.

Figure 3:
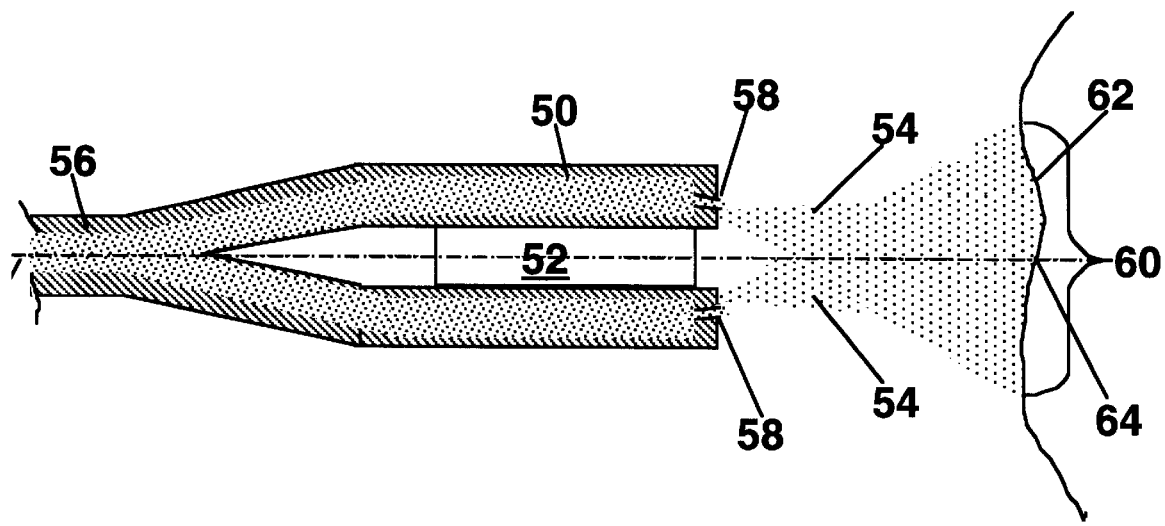
FIG. 3 shows a cross-sectional view of an alternative embodiment of the temperature sensor and nozzle to provide coaxial operation.

FIG. 3 shows a cross-sectional side view of an alternative embodiment of a nozzle 50 and temperature sensor 52 assembly. This embodiment ensures that the temperature sensor 52 measures or samples along the same axis 66 as the cone or field of view of the mist 54 produced, that is, the sensor 52 and center of the mist pattern 60 are coaxial, or substantially parallel. The cryogenic fluid is delivered through a tube 56 to atomizing orifices 58. The orifices 58 are arranged around the end of the annular nozzle 50 to create a mist 54 that uniformly covers an area 60 on the surface 62. The non-contact temperature sensor 52 is located in the center of the annular nozzle 50 and samples the temperature around the center 64 of the cooled area 60.

Figure 4:
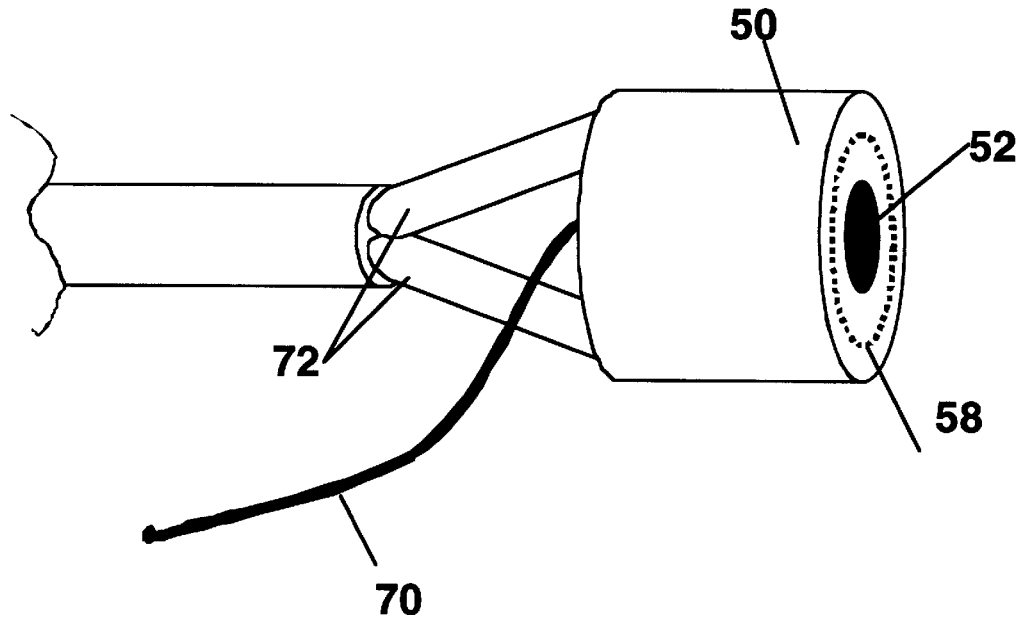
FIG. 4 shows a side elevation of the embodiment of FIG. 3.

FIG. 4 shows a side elevation view of the coaxial nozzle 50 and temperature sensor 52 assembly. The array of orifices 58 are evenly distributed in at least one circular pattern on nozzle 50. The number of orifices (or size of array) is adjusted to control the size of the area to be uniformly cooled. The electronic cable 70 exits the sensor 52 between the tubes 72, which deliver fluid to the atomizing nozzle 50, and connects to the control unit.

The cooling rate of this device will depend on the amount of cryogenic mist that hits the surface. For faster rates it's important that liquid droplets reach the surface. Upon striking the surface the drops will quickly vaporize and draw heat away from the surface. The thin vapor layer will form an insulating layer that limits the amount of heat removed per drop. This effect along with the small drop size is important to prevent necrosis if the user is cooling human tissue. For uniform cooling the area cooled by the stream of droplets from adjacent nozzle orifices should overlap as the user operates the device. This can be achieved by having the orifices spaced 2–5 droplet diameters (typically 0.2–5 mm) apart. Alternatively, the user can move the device over a distance of at least one orifice spacing to improve uniformity. An acoustic or mechanical vibrating device could be incorporated into the nozzle section to automatically perform this function.

The above descriptions and illustrations are only by way of example and are not to be taken as limiting the invention in any manner. It is obvious that one skilled in the art can substitute known equivalents for the structures and means described. The full scope and definition of the invention, therefore, is set forth in the following claims.

What is claimed is:

1. A device for cooling a surface to a desired temperature, comprising:
    a reservoir for a cryogenic fluid having a valve to controllably release the fluid from the reservoir;
    means to form a mist of the fluid released from the reservoir and to direct the mist at the surface to cool an area;
    a non-contact temperature sensor that measures the temperature of the surface within the cooled area; and
    a control unit connected to the temperature sensor that activates the temperature sensor, wherein the control unit can be programmed by a user with the desired final temperature.

2. A device as recited in claim 1, wherein the control unit continuously displays the measured temperature of the cooled area.

3. A device as recited in claim 1, wherein the control unit generates a visual or audible signal when the surface temperature reaches the desired temperature.

4. A device as recited in claim 1, wherein the means to form the mist comprises a nozzle having one or more orifices.

5. A device as recited in claim 1, wherein the temperature sensor is selected from the group consisting of infrared sensors and fluorescence sensors.

6. A device as recited in claim 1, further comprising an optical source connected to the control unit that produces a beam of light that illuminates at least a point in the cooled area.

7. A device as recited in claim 1, wherein the valve is activated electronically.

8. A method for cooling a surface to a desired temperature, comprising:
    directing a mist of a cryogenic fluid at the surface to cool an area;
    activating a non-contact temperature sensor using a control unit;
    measuring the temperature of the surface within the cooled area with the temperature sensor; and
    stopping the mist when the measured temperature reaches the desired temperature.

9. A method as recited in claim 8, further comprising continuously displaying the measured temperature of the cooled area.

10. A method as recited in claim 8, wherein the surface is human tissue.

11. A method as recited in claim 8, wherein the cryogenic fluid is selected from the group consisting of nitrogen, xenon, and neon.

12. A method as recited in claim 8, wherein stopping the mist is carried out automatically by the control unit sending an electronic signal that activates a valve through which the fluid flows to close.

13. A method as recited in claim 8, further comprising programming the control unit with the desired temperature.

14. A method as recited in claim 8, further comprising generating a visual or audible signal by the control unit when the surface temperature reaches the desired temperature.

15. A method as recited in claim 8, further comprising illuminating at least a point in the cooled area using a beam of light from an optical source connected to the control unit.

16. A device for cooling a surface to a desired temperature, comprising:
    a reservoir for a cryogenic fluid having a valve to controllably release the fluid from the reservoir;
    means to form a mist of the fluid released from the reservoir and to direct the mist at the surface to cool an area;
    a non-contact temperature sensor that measures the temperature of the surface within the cooled area; and
    a control unit connected to the temperature sensor that activates the temperature sensor, wherein the valve is connected to the control unit, and the control unit activates the valve to close when the surface temperature reaches the desired temperature.

17. The device as recited in claim 16, wherein the control unit continuously displays the measured temperature of the cooled area.

18. A device as recited in claim 16, wherein the means to form the mist comprises a nozzle having one or more orifices.

19. A device as recited in claim 16, wherein the temperature sensor is selected from the group consisting of infrared sensors and fluorescence sensors.

20. A device as recited in claim 16, further comprising an optical source connected to the control unit that produces a beam of light that illuminates at least a point in the cooled area.

21. A device as recited in claim 16, wherein the valve is activated electronically.

22. A device for cooling a surface to a desired temperature, comprising:
    a reservoir for a cryogenic fluid having a valve to controllably release the fluid from the reservoir;
    means to form a mist of the fluid released from the reservoir and to direct the mist at the surface to cool an area;

a non-contact temperature sensor that measures the temperature of the surface within the cooled area; and a control unit connected to the temperature sensor that activates the temperature sensor, wherein the mist is directed along a first axis, and the temperature sensor measures the temperature of the cooled area along a second axis, wherein the first and second axes are coaxial.

23. The device as recited in claim 22, wherein the control unit continuously displays the measured temperature of the cooled area.

24. A device as recited in claim 22, wherein the means to form the mist comprises a nozzle having one or more orifices.

25. A device as recited in claim 22, wherein the temperature sensor is selected from the group consisting of infrared sensors and fluorescence sensors.

26. A device as recited in claim 22, further comprising an optical source connected to the control unit that produces a beam of light that illuminates at least a point in the cooled area.

27. A device as recited in claim 22, wherein the valve is activated electronically.

28. A device for cooling a surface to a desired temperature comprising:

a reservoir for a cryogenic fluid having a valve to controllably release the fluid from the reservoir;

means to form a mist of the fluid released from the reservoir and to direct the mist at the surface to cool an area;

a non-contact temperature sensor that measures the temperature of the surface within the cooled area; and a control unit connected to the temperature sensor that activates the temperature sensor, wherein the valve is activated mechanically.

29. The device as recited in claim 28, wherein the control unit continuously displays the measured temperature of the cooled area.

30. A device as recited in claim 28, wherein the means to form the mist comprises a nozzle having one or more orifices.

31. A device as recited in claim 28, wherein the temperature sensor is selected from the group consisting of infrared sensors and fluorescence sensors.

32. A device as recited in claim 28, further comprising an optical source connected to the control unit that produces a beam of light that illuminates at least a point in the cooled area.

33. A device as recited in claim 28, wherein the valve is activated electronically.

34. A device for cooling a surface to a desired temperature, comprising:

a reservoir for a cryogenic fluid having a valve to controllably release the fluid from the reservoir;

means to form a mist of the fluid released from the reservoir and to direct the mist at the surface to cool an area;

a non-contact temperature sensor that measures the temperature of the surface within the cooled area; and a control unit connected to the temperature sensor that activates the temperature sensor, wherein the control unit further comprises a display for displaying the desired temperature and an interface for a user to set the desired temperature.

35. The device as recited in claim 34, wherein the control unit continuously displays the measured temperature of the cooled area.

36. A device as recited in claim 34, wherein the means to form the mist comprises a nozzle having one or more orifices.

37. A device as recited in claim 34, wherein the temperature sensor is selected from the group consisting of infrared sensors and fluorescence sensors.

38. A device as recited in claim 34, further comprising an optical source connected to the control unit that produces a beam of light that illuminates at least a point in the cooled area.

39. A device as recited in claim 34, wherein the valve is activated electronically.

* * * * *